United States Patent [19]
Goodman et al.

[11] Patent Number: 5,241,049
[45] Date of Patent: Aug. 31, 1993

[54] NEUTROPHIL CHEMOATTRACTANTS

[75] Inventors: Richard B. Goodman, Kirkland; John W. Forstrom, Seattle; Thomas R. Martin, Mercer Island, all of Wash.

[73] Assignee: ZymoGenetics, Inc., Seattle, Wash.

[21] Appl. No.: 455,698

[22] Filed: Dec. 22, 1989

[51] Int. Cl.⁵ ..................... A61K 37/02; C07K 3/02; C07K 15/06
[52] U.S. Cl. ................................. 530/350; 530/300
[58] Field of Search ............. 530/300, 324, 350, 848; 514/12, 21

[56] References Cited

FOREIGN PATENT DOCUMENTS

| WO89/04325 | 5/1989 | PCT Int'l Appl. |
| WO89/04836 | 6/1989 | PCT Int'l Appl. |
| WO89/08665 | 9/1989 | PCT Int'l Appl. |
| WO89/10962 | 11/1989 | PCT Int'l Appl. |

OTHER PUBLICATIONS

Golds et al, "Inflammatory cytokines induce synthesis and secretion of gro protein and a neutrophil chemotactic factor . . . ". Biochem. J. (1989) 259, 585–88.

Gregory et al. "Structure Determination of a Human Lymphocyte Derived Neutrophil Activity Peptide", Biochem. Biophys. Res. Comm. vol. 151, No. 2, 1988, pp. 883–890.

Walz et al, "Purification and Amino Acid Sequencing of NAF . . . ", Biochem. Biophys. Res. Comm. vol. 149, No. 2, 1987, pp. 755–761.

Matsushima et al, "Molecular Cloning of a Human Monocyte-Derived Neutrophil Chemotactic Factor . . . " J. Exp. Med., vol. 167, Jun. 1988, pp. 1883–1893.

Suzuki et al, "Purification and Partial Primary Sequence of a Chemotactic Protein for Polymorphonuclear Leukocytes . . . ", J. Exp. Med. vol. 169, Jun. 1989, pp. 1895–1901.

Schroder et al, "Identification of Different Charged Species of a Human Monocyte Derived Neutrophil Activating peptide (MONA)", Biochem. Biophys. Res. Comm. 152:277–284, 1988.

Wolpe et al, "Identification and characterization of macrophage inflammatory protein 2", Proc. Natl. Acad. Sci. USA 86:612–616, 1989.

Strieter et al., "Endothelial Cell Gene Expression of a Neutrophil Chemotactic Factor by TNF-a, LPS, and IL-β", Science 243:1467–1469, 1989.

Primary Examiner—Jeffrey E. Russel
Attorney, Agent, or Firm—Seed and Berry

[57] ABSTRACT

Substantially pure porcine proteins having chemoattractant activity for neutrophils and methods for preparing the proteins are provided. These proteins are useful within compositions for enhancing neutrophil chemotaxis, such as in promoting the formation of granulation tissue. The proteins may also be used within methods for developing inflammatory and anti-inflammatory agents.

3 Claims, 6 Drawing Sheets

| | 1 | 10 | 20 |
|---|---|---|---|
| pAMCP-I | ARVSABL | CRQCINTHSTPPH | ... |
| pAMCP-II | SPIEAAEAAVVRELRC | MCLTTTPGI | HPKM I... |
| hIUCT | AVLPRSAKELCC | CRQCIKTYSKPF | HPKK FI... |
| hNAP-1 | AVLPRSAKELRC | QCIKTYSKPF | HPKF I... |
| hPF-4 | EAEEDGDLQCC | LCVKTTSQVRPRH | I... |
| rPF-4 | VTRASPEESDGDLSCC | VCVKTTSSRIHLKR | I... |
| bPF-4 | ...PLPADSEGGEDEDLQCC | VCLKTTSGINPRH | I... |
| mMIP-2 | AVVASELRC | QCLKTLPRVDF KN | I... |
| hPBP | ...GKEESLDSDLYA*ELRC | MCIKTTSGIHPKN | I... |
| C9E3 | ...LSQGRTLVKMGNELRC | QCISTHSKFIHPKS | I... |
| hGro | RRAAGASVATELRC | QCLQTLQG IHPKN | I... |

FIG. 6

NEUTROPHIL CHEMOATTRACTANTS

Development of this invention was supported in part by the medical research service of the Veteran's Administration and by National Institutes of Health grants HL 30542, HL 33247 and AI 29103. The government has certain rights in this invention.

TECHNICAL FIELD

The present invention relates generally to chemotactic proteins and, more specifically, to proteins chemotactic for human neutrophils, methods for producing these proteins, and therapeutic compositions containing the proteins.

BACKGROUND OF THE INVENTION

Inflammation is the reaction of living tissue to infection or injury, normally resulting in healing and the restoration of tissue structure and function. Inflammation also involves a complex set of responses which neutralize and remove pathogens and lead to the repair of the affected area. Symptoms of inflammation include pain, heat, redness, swelling, and dysfunction. Vascular dilation occurs, together with exudation of fluid and certain cellular components of blood into the surrounding tissue.

Most inflammatory states are characterized by the presence of neutrophils, or polymorphonuclear leukocytes (PMN).

Inflammation occurs in the initial stages of wound healing and is an integral part of the wound-healing process. Inflammation promotes the formation of granulation tissue. The earliest steps in this inflammatory response involve the influx of neutrophils into the wound space. Although PMN are important in phagocytizing wound debris and bacterial contaminants, their exact role in wound healing is unclear.

Inflammation is also associated with a number of disease states. In some diseases, such as pneumonia, inflammation is important to eradication of infection and ultimate survival of the patient. In other diseases, unchecked inflammation may be detrimental, probably due to tissue injury caused by the oxidants and proteolytic enzymes released by PMN. In these latter conditions, a reduction in inflammation is beneficial to the patient. Examples of such disease states include arthritis and other inflammatory joint diseases, adult respiratory distress syndrome and idiopathic pulmonary fibrosis.

Lung inflammation is characterized by the presence of PMN in the pulmonary interstitium and airspaces. For example, interstitial and airspace neutrophils are a hallmark of adult respiratory distress syndrome (ARDS) (Pistorese et al., *Chest* 88: A86, 1985; Maunder et al., *Am. Rev. Resoir. Dis.* 135: A260, 1987). Severity of ARDS is proportional to the number of neutrophils in the lungs, and patients who have fewer airspace neutrophils relative to airspace macrophages have a better rate of survival (Maunder et al., *Am. Rev. Respir. Dis.* 139: A221, 1989). Neutrophil influx also appears to be involved in the pathogenesis of idiopathic pulmonary fibrosis (IPF) (Bitterman et al., *J. Clin. Invest.* 72: 1801–1813, 1983; Hunninghake et al., *J. Clin. Invest.* 68: 259–269, 1981).

A major role for neutrophils in the symptoms of inflammation is suggested by studies of Job's syndrome, a congenital defect in PMN chemotaxis (Hill et al., *Lancet* 2: 617–619, 1974). Patients with this condition experience recurrent "cold abscesses" without the usual associated symptoms of inflammation. In addition, patients with diabetes mellitus and patients receiving corticosteroid therapy have impaired response to infection, which may be related to impaired PMN chemotaxis.

Two classes of chemotactically active molecules that can recruit PMN from the bloodstream into the lungs have been identified. A low molecular weight human lipid was identified by Hunninghake et al. (*J. Clin. Invest.* 66: 473–483, 1980), and has subsequently been identified as leukotriene $B_4$ ($LTB_4$) (Martin et al., *Am. Rev. Respir. Dis.* 129: 106–111, 1984; Martin et al., *J. Clin. Invest.* 80: 1114–1124, 1987). A protein with a molecular weight of approximately 10,000 Daltons produced by human alveolar macrophages has been described (Merrill, et al., *J. Clin. Invest.* 65: 268–276, 1980) but has not been precisely identified or characterized.

Recently, four different groups have isolated homologous low molecular weight (6–10 kDa) peptide chemoattractants from LPS-stimulated human peripheral blood monocytes (Yoshimura et al., *J. Immunol.* 139: 788–793, 1987; Schroder et al., *J. Immunol.* 139: 3474–3483, 1987; Yoshimura et al., *Proc. Natl. Acad. Sci. USA* 84: 9233–9237, 1987; Matsushima et al., *J. Exp. Med.* 167: 1883–1893, 1988; Walz et al., *Biochem. Biophys. Res. Comm.* 149: 755–761, 1987; Thelen et al., *FASEB J.* 2: 2702–2706, 1988; Peveri et al., *J. Exp. Med.* 167: 1547–1549, 1988; Lindley et al., *Proc. Natl. Acad. Sci. USA* 85: 9199–9203, 1988; Van Damme et al., *J. Exp. Med.* 167: 1364–1376, 1988; Schroder et al., *Biochem. Biophys. Res. Comm.* 152: 277–284, 1988) that are identical to the amino acid sequence inferred from the 3-10C cDNA sequence reported by Schmid et al., (*J. Immunol.* 139: 250–256, 1987). The protein has now been called NAP-1.

Experimental evidence suggests that the production of particular chemoattractants is determined by the nature and duration of the inflammatory stimulus. Thus, efforts to control the production or activity of only one of these chemoattractants (e.g. $LTB_4$) may be ineffective in regulating an inflammatory response.

There remains a need in the art for substances that can either promote or reduce inflammation. Those that promote inflammation may find utility in speeding the healing of wounds or aiding recovery from pneumonia. Promotion of inflammation may be particularly desirable in patients with defects in PMN chemotaxis, including diabetics, patients receiving steroid therapy, and patients with congenital chemotaxis defects (e.g. Job's syndrome). Anti-inflammatory agents would find utility in the treatment of certain inflammatory lung diseases. Because alveolar macrophage-derived chemoattractants are likely to be important in mediating neutrophil migration and the resultant lung injury, efforts to interrupt this inflammatory process would require an understanding of all mechanisms of neutrophil chemotaxis.

DISCLOSURE OF THE INVENTION

The present invention provides substantially pure porcine alveolar macrophage-derived chemotactic factor I (AMCF-I). In one embodiment, the AMCF-I has the amino-terminal amino acid sequence Ala-Arg-Val-Ser-Ala-Glu-Leu-X-Arg-Gln-X-Ile-Asn-Thr-His-Ser-Thr-Pro-Phe-His, wherein X is Cys or another amino acid. In another embodiment, AMCF-I with a specific activity of at least about 200,000 units/mg is provided. In a further embodiment, the present invention provides AMCF-I with a specific activity of at least 400,000 units/mg.

In another aspect, the present invention provides substantially pure porcine alveolar macrophage-derived chemotactic factor II (AMCF-II). In one embodiment, the AMCF-II has the amino-terminal amino acid sequence Ser-Pro-Ile-Glu-Ala-Ala-Glu-Ala-Ala-Val-Val-Arg-Glu-Leu-Arg-X-Met-X-Leu-Thr-Thr-Thr-Pro-Gly-Ile-His-Phe-Lys-Met-Ile, wherein X is Cys or another amino acid. In another embodiment, AMCF-II with a specific activity of at least about 100,000 units/mg is provided. In yet another embodiment, the present invention provides AMCF-II with a specific activity of at least 200,000 units/mg.

In a related aspect, the present invention provides a protein composition comprising porcine AMCF-I and AMCF-II, the composition having a specific activity of at least about 20,000 units/mg.

The present invention further provides compositions comprising the substantially pure proteins and protein compositions described above in combination with a physiologically acceptable carrier or diluent.

In another aspect, the present invention provides isolated DNA molecules encoding AMCF-I or AMCF-II.

In yet another aspect, the present invention provides methods for preparing a chemotactic protein composition. The methods generally comprise the steps of (a) stimulating cells selected from the group consisting of porcine monocytes and porcine macrophages with a septic mediator such as bacterial endotoxin; (b) culturing the stimulated cells to produce a cell-conditioned medium; (c) concentrating the cell-conditioned medium; (d) chromatographically separating the concentrated medium under acidic conditions to produce a fraction having chemotactic activity for human neutrophils and a fraction substantially free of chemotactic activity for human neutrophils; and (e) recovering the fraction having chemotactic activity. In a preferred embodiment, the cells are porcine alveolar macrophages. In another embodiment, the cell-conditioned medium is acidified prior to concentrating, and the concentrating step comprises cation exchange chromatography. In a particularly preferred embodiment, the proteins are further purified by chromatographically fractionating the recovered fraction having chemotactic activity of step (e) to produce one or more chemotactically active fractions and a fraction substantially free of chemotactic activity, and recovering at least one of the chemotactically active fractions. The fractionating step may comprise reversed-phase high-performance liquid chromatography.

These and other aspects of the invention will become evident upon reference to the following detailed description and attached drawings.

BRIEF DESCRIPTION OF THE DRAWINGS

FIG. 6 is a comparison of the amino-terminal amino acid sequences of AMCF-I and AMCF-II with related polypeptides. Lower case letters designate species: p, porcine; h, human; r, rat; b, bovine; m, mouse; c, chicken. * indicates the N-terminal alanine residue of the platelet basic protein cleavage, NAP-2.

BEST MODE FOR CARRYING OUT THE INVENTION

Figure 1:
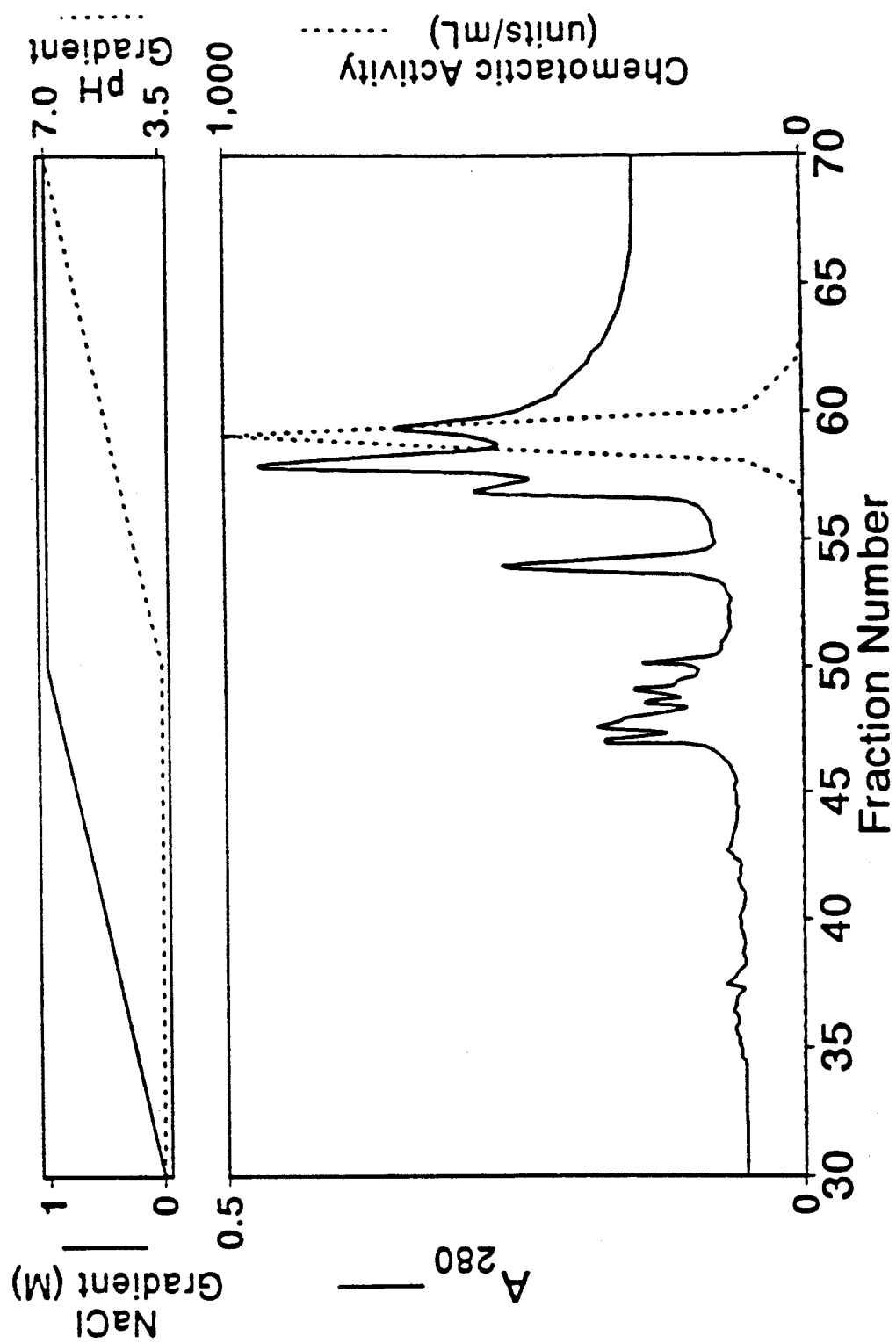
FIG. 1 is a cation exchange HPLC purification profile of a chemotactic protein composition of the present invention. The elution gradient program is shown in the top panel.

Prior to setting forth the invention, it may be helpful to an understanding thereof to set forth definitions of certain terms to be used hereinafter.

Specific Activity: For AMCF-I and AMCF-II, specific activity is defined as units of chemotactic activity per mg of protein. One unit of chemotactic activity is the amount of a sample required to give at least three times the baseline (negative control) activity in a chemotaxis assay using human neutrophils as described herein. Total protein in a sample is determined by the Folin phenol method (Lowry et al., *J. Biol. Chem.* 193: 265-275, 1951), by absorbance at 280 nm ($A_{280}$ of a 1.0 mg/ml solution=1.000), or by quantitative amino acid analysis.

Substantially Pure: Greater than 90% pure (on the basis of total protein) as determined by SDS-polyacrylamide gel electrophoresis, reversed-phase HPLC, or quantitative amino acid sequence analysis.

The inventors have isolated and characterized a class of novel proteins from LPS-stimulated porcine alveolar macrophages. These proteins have potent chemotactic activity for polymorphonuclear leukocytes and, as such, are useful for enhancing inflammation. The proteins also provide useful tools for the discovery of anti-inflammatory compounds.

The proteins of the present invention have been designated as "alveolar macrophage-derived chemotactic factors". Two of these proteins are hereinafter referred to as AMCF-I and AMCF-II. These proteins have been produced in a substantially pure form having a high specific activity as measured in a chemotaxis assay using human neutrophils. Both have a molecular weight of approximately 10 kDa as determined by polyacrylamide gel electrophoresis. The amino acid compositions of these proteins are presented below in Table 3. As will be appreciated by those skilled in the art, these compositions are approximate and may vary somewhat from preparation to preparation, and may also vary depending upon the source of the protein and the particular analytical methods employed. Although other specific properties of AMCF-I and AMCF-II are disclosed herein, including representative partial amino acid sequences, the invention also includes similar chemotactically active porcine proteins having slight variations in amino acid sequence or other properties. Such variations may arise naturally (e.g. due to genetic polymorphism) or may be produced by human intervention (e.g. by mutagenesis of cloned DNA sequences).

According to the present invention, the proteins of the present invention can be isolated from porcine macrophages or monocytes. A particularly preferred starting material is porcine alveolar macrophages, which may be obtained by lung lavage. The isolated cells are stimulated by culturing them according to standard cell culture methods in the presence of a mediator of sepsis. Suitable mediators include bacterial endotoxin (LPS) and the cytokines IL-1 and TNF. The resulting conditioned culture medium is recovered and used as the source of the proteins.

The cell-conditioned medium is concentrated by conventional techniques, such as ultrafiltration, dialysis, salt precipitation, ion exchange chromatography, affinity chromatography or lectin adsorption. A particularly preferred method of concentration is cation exchange chromatography under acidic conditions. A particularly preferred cation exchange medium in this regard is sulfopropyl-derivatized dextran, such as SP-Sephadex C-25, available from Pharmacia, Piscataway, N.J. The conditioned medium is combined with the cation exchange medium in a solution having a pH of about 2.0 to 7.0, preferably about 3.5. The column is washed to remove unbound material, then the bound material is eluted using a high salt buffer at about neutral pH. A particularly preferred such buffer is 100 mM potassium phosphate buffer pH 7.0 containing 1.0 M NaCl. Prior to concentration, it is advantageous to clarify the conditioned medium, such as by centrifugation or filtration. To minimize proteolysis, concentration is preferably carried out at low temperature, e.g. about 5° C.

The concentrated medium is then chromatographically separated to isolate the chemotactically active proteins from other components. Prior to chromatography it is preferable to reduce the salt concentration of the concentrated medium, such as by dialysis against a low ionic strength, acidic buffer such as 10 mM acetic acid/Na acetate buffer, pH 3.5. In any event, the medium is preferably acidified prior to fractionation. The medium is then separated into active and inactive fractions by high performance liquid chromatography on a cation exchange resin. A preferred such resin is sulfopropyl-derivatized silica, such as TSK SP-5PW (Bio-Rad Laboratories, Richmond, Calif.). Alternatively, separation may be achieved by conventional liquid chromatography on a cation exchange resin. The column is washed with a pH gradient, and chemotactically active fractions are recovered. Prior to washing the column with the pH gradient, it is preferred to elute contaminating proteins from the column with a salt gradient. The resulting composition is a partially purified mixture containing AMCF-I and AMCF-II and having a specific activity typically greater than about 20,000 units/mg.

Additional purification and separation of AMCF-I and AMCF-II is achieved by chromatographically fractionating the chemotactically active mixture. Preferred chromatographic methods include reversed-phase high performance liquid chromatography and molecular seive chromatograhy. A preferred HPLC medium in this regard is Vydac C-4 large pore silica (The Separations Group, Hesperia, Calif.). It is preferred to acidify the partially purified, active mixture prior to chromatographically fractionating it, such as by dialysis against a low pH buffer. A particularly preferred dialysis buffer is 10 mM acetic acid/Na acetate, pH 3.5. In a particularly preferred embodiment, the preparation is then applied to an HPLC column, which is eluted with a gradient of an organic solvent such as acetonitrile. Column fractions are assayed for chemotactic activity, and active fractions are retained. AMCF-I and AMCF-II typically elute at about 35%–45% acetonitrile under these conditions.

The purification process may be monitored throughout by assaying the chemotactic activity and protein content of the preparation. Chemotactic activity is preferably assayed according to standard procedures using human neutrophils. Protein content of the preparation may be monitored by absorption at 280 nm, polyacrylamide gel electrophoresis, quantitative analytical techniques, or other methods known in the art.

The proteins of the present invention may also be produced by expressing cloned DNA sequences (cDNA is preferred) in recombinant cells. A suitable cDNA may be isolated from a porcine alveolar macrophage cDNA library. Suitable libraries may be prepared according to standard procedures. In a preferred method, a porcine alveolar macrophage cDNA expression library is screened using affinity-purified antibodies (Young and Davis, *Proc. Natl. Acad. Sci. USA* 80: 1194–1198, 1983; Davis et al., U.S. Pat. No. 4,788,135). Partial cDNA clones (fragments) can be extended by re-screening of the library with the cloned cDNA fragment until the full sequence is obtained. Additional methods of cDNA cloning are also suitable, including screening cDNA libraries with oligonucleotide probes designed on the basis of N-terminal amino acid sequences disclosed herein or the sequences of CNBr fragments from isolated proteins. Additional cloning methods are described by Maniatis et al., eds. (*Molecular Cloning: A Laboratory Manual*, Cold Spring Harbor Laboratory, Cold Spring Harbor, N.Y., 1982) which is incorporated herein by reference. The identities of cloned sequences are confirmed by sequencing or activity assays of expressed clones.

For expression in recombinant host cells, a DNA sequence encoding a chemoattractant protein is inserted into a suitable expression vector. Expression vectors useful in this regard contain transcriptional promoter and terminator sequences operably linked to the DNA sequence to be expressed. Depending on the particular host cell selected, expression vectors may also contain an origin of replication, enhancer sequences, and other nucleotide sequences which regulate or enhance expression levels. In many instances it is advantageous to include a bacterial origin of replication so that the vector can be replicated and manipulated using a prokaryotic host. Selectable markers, sequences which provide for the selection and maintenance of the vector in the host cell, may also be provided in the expression vector, although in some cases a selectable marker may be introduced into the host cell on a separate vector. Suitable expression vectors may be derived from plasmids or viruses, or may contain elements of both. Selection of the appropriate elements and construction of vectors is within the ordinary level of skill in the art.

Higher eukaryotic cells (such as mammalian and insect cells) are preferred as host cells within the present invention. Expression vectors for use in mammalian cells comprise a promoter capable of directing the transcription of a cloned gene or cDNA introduced into a mammalian cell. Suitable promoters include cellular promoters, such as the mouse metallothionein-1 (MT-1) promoter (Palmiter et al. *Science* 222: 809–814, 1983 and U.S. Pat. No. 4,579,821), and viral promoters, such as the SV40 (Subramani et al., *Mol. Cell. Biol.* 1: 854-864, 1981) promoter and the major late promoter of adenovirus 2 (Berkner and Sharp, *Nuc. Acids Res.* 13: 841-857, 1985). Also included in such expression vectors is a polyadenylation signal, located downstream of the DNA sequence insertion site. The polyadenylation signal may be that of the DNA sequence of interest, or may be derived from a heterologous gene.

Expression vectors are introduced into cultured mammalian cells according to standard procedures, for example, calcium phosphate-mediated transfection (Wigler et al., *Cell* 14: 725, 1978; Corsaro and Pearson, *Somat. Cell Genet.* 7: 603, 1981; Graham and Van der Eb, *Virol.* 52: 456, 1973) or electroporation (Neumann et al., *EMBO J.* 1: 841-845, 1982). A small fraction of the treated cells integrate the DNA into their genomes or maintain the DNA in non-chromosomal nuclear structures. In order to identify these integrants, a selectable marker is generally introduced into the cells along with the gene of interest. Preferred selectable markers include genes that confer resistance to drugs such as neomycin, hygromycin, and methotrexate. Selectable markers may be introduced into the cell on a separate expression vector at the same time as the gene of interest, or they may be introduced on the same expression vector.

The copy number of the integrated gene sequences may be increased through amplification by using certain selectable markers (e.g., a dihydrofolate reductase gene, which confers resistance to methotrexate). The selectable marker is introduced into the cells along with the gene of interest, and drug selection pressure is applied. By selecting for increased copy number of cloned sequences, expression levels may be substantially elevated.

Cells of lower organisms may also be used within the present invention. In this regard, a particularly preferred host is the yeast *Saccharomyces cerevisiae*, although other fungal cells may also be used. For recombinant proteins that require disulfide bonding and/or glycosylation for biological activity, or to facilitate purification of a recombinant protein, a secretory expression system is used. The DNA sequence encoding the protein of interest is fused, in the correct reading frame, to a sequence encoding a secretory signal peptide (a "signal sequence"). Particularly preferred signal sequences include those encoding the pre-pro region of the MFα1 (yeast alpha-factor) gene product (Kurjan and Herskowitz, *Cell* 30: 933-943, 1982; Singh, EP 123,544; and Kurjan et al., U.S. Pat. No. 4,546,082) and the secretory peptide portion of the BARI gene (MacKay et al., U.S. Pat. No. 4,613,572 and MacKay, WO 87/02670). The BAR1 signal sequence may be combined with the coding sequence for the third domain of the BARI gene product (MacKay et al., EP 314,096). Other useful signal sequences include those of the yeast PH05 (Lemontt et al., WO 86/00638) and a-factor (Brake, EP 123,289) genes.

Techniques for transforming yeast are well known and have been described by, for example, Beggs (*Nature* 275: 104-108, 1978) and Hinnen (*Proc. Natl. Acad. Sci. U.S.A.* 81: 1740-1747, 1984). Suitable expression vectors include YRp7 (Struhl et al., *Proc. Natl. Acad. Sci. U.S.A.* 76: 1035-1039, 1979), YEp13 (Broach et al., *Gene* 8: 121-133, 1979), pJDB248 and pJDB219 (Beggs, ibid.), and derivatives thereof. Such vectors generally include a selectable marker. A defective selectable marker, such as the leu2-d gene of Beggs (ibid.) or the POT1 gene of Kawasaki and Bell (EP 171,142), is particularly preferred. Preferred promoters useful in yeast expression vectors include promoters from yeast glycolytic genes (Hitzeman et al., *J. Biol. Chem.* 255: 12073-12080, 1980; Alber and Kawasaki, *J. Mol. Appl. Genet.* 1: 419-434, 1982; and Kawasaki, U.S. Pat. No. 4,599,311) or alcohol dehydrogenase genes, particularly the ADH2-4c promoter (also known as "ADR3-4c;" see Russell et al., *Nature* 304 652-654, 1983). Hybrid promoters may also be utilized as disclosed by Bitter (WO 86/06077) and Rosenberg et al. (Ep 164,556). Hybrid promoters can also be constructed as disclosed in U.S. patent application Ser. No. 07/036,823 by inserting one or more copies of a yeast mating-type regulatory element into a yeast promoter.

The transformed or transfected host cells are grown in a culture medium containing carbon and nitrogen sources and appropriate supplements. Selection of culture media appropriate for a particular cell type is within the level of ordinary skill in the art. The protein may be isolated from the cells or culture media as generally described above.

The proteins of the present invention may be used within therapeutic compositions for the treatment of a broad spectrum of wounds. Types of wounds that may be treated with these proteins include superficial wounds and lacerations, abrasions, surgical wounds and burns. In general, these proteins will be useful in any condition where the formation of granulation tissue is desired. In addition to the above wounds, such conditions include skin grafts and treatment with artificial skin.

For therapeutic use, it is preferred to administer the proteins topically in combination with a physiologically acceptable carrier or diluent. The protein will be prepared so as to be free of toxic or pyrogenic substances. The composition will be delivered in a volume sufficient to cover the wound. Compositions will be formulated to provide a concentration of the active protein of between about $10^{-12}M$ to $10^{-4}M$ within the wound space. These compositions will generally be reapplied at one- to several-day intervals until granulation tissue formation is substantially complete. The exact treatment regimen will be determined by the size and nature of the wound and the overall condition of the patient. In severe cases, it may be necessary to administer the therapeutic compositions of the present invention more frequently, i.e. up to four times per day, and for longer duration.

Therapeutic compositions according to the present invention comprise the proteins described herein in combination with suitable carriers, as well as adjuvants, diluents, or stabilizers. Typically, the proteins described herein will be used in a concentration of about $10^{-8}M$ to $10^{-5}M$, although concentrations in the range of $10^{-12}M$ to $10^{-4}M$ may be used. Diluents include albumins, saline, sterile water, mannitiol, etc. Other stabilizers, antioxidants, or protease inhibitors may also be added. Other optional ingredients include growth factors, such as platelet-derived growth factor (PDGF), basic fibroblast growth factor (bFGF), epidermal growth factor (EGF), insulin-like growth factor 1 (IGF-1), etc., and monocyte chemoattractant. Alternatively, the proteins may be applied to wound dressings as aqueous solutions, and the dressings may be packaged in sterile form.

For treatment of pneumonia, the proteins of the present invention are combined with a suitable carrier and formulated for bronchial or intravenous delivery. Bronchial delivery may be via nebulization or via a bronchoscope. Suitable carriers and diluents for bronchial delivery include sterile, pyrogen-free saline with a suitable protein carrier, such as albumin. Suitable diluents for intravenous administration include sterile water and sterile saline. The proteins are formulated to provide a dose concentration of from about $10^{-12}$M to $10^{-4}$M, more preferably $10^{-8}$M to $10^{-5}$M.

The proteins of the present invention may also be used systemically to block localized inflammation. In this regard, the proteins are formulated as aqueous solutions and administered intravenously as described above.

In addition, the proteins of the present invention are useful tools for the development of anti-inflammatory agents. A wide variety of anti-inflammatory agents may be developed, including blocking antibodies, peptide antagonists, and small, non-peptide antagonists. For example, antibodies against the proteins or their cellular receptors may be used to block their chemotactic activity. Analysis of the amino acid sequences and structure-function relationships of the proteins provides guidance for the synthesis of small peptides related to the active sites (receptor binding sites). Of particular interest are the regions around amino acids 12-18 of AMCF-I and amino acids 19-25 of AMCF-II (see FIG. 6). Peptides that mimic the binding of the proteins to their receptors without triggering chemotaxis are useful in blocking PMN chemotaxis and thus reducing inflammation. Finally, the chemotaxis assay systems described hereinafter may be adapted to screen for anti-chemotactic agents. By adding a test compound to the assay, the ability of that compound to block the activity of the proteins is determined.

Fragments of the proteins of the present invention may also be used to promote inflammation. As described above, the sequences of the proteins are analyzed to determine the active sites, and small peptides containing an active site sequence are prepared and assayed for chemotactic activity. Small peptides may also be produced by other conventional methods, such as proteolytic digestion of the intact proteins or expression of small DNA molecules in recombinant cells.

EXAMPLES

Example 1—Purification of AMCF-I and AMCF-II 20-30 kg male Yorkshire pigs were obtained from Latch Farms, North Bend, Wash. and used as a source of both AM and PMN. Porcine AM were obtained by whole lung lavage. Pigs were sedated with an intramuscluar injection of 250 mg of ketamine and 100 mg of xylazine and then euthanized with intravenous sodium penthothal. With the animals supine, the chest was opened with a median sternotomy to allow free collapse of the lungs. The trachea was isolated, incised, and intubated with a #7 cuffed endotracheal tube. The cuff was inflated in the trachea and sterile pyrogen free 0.9% NaCl containing 50 mM EDTA was instilled into the airways to a hydrostatic pressure of 30 cm $H_2O$ (approximately 2 liters). The cell-enriched fluid was collected by gravity drainage. This lavage procedure was repeated twice on each animal. An average pig lung lavage yielded $2.7 \times 10^9 \pm 1.3 \times 10^9$ (mean±S.D.) viable AM, with a purity of 96%±1.5% AM, 2%±0.8% lymphocytes and 1%±0.4% PMN. AM viability always exceeded 90% by trypan blue dye exclusion.

The lavage fluids were spun at 200 x G for 15 minutes to pellet the cells. The cell pellets were washed twice with sterile pyrogen-free 0.9% NaCl, and resuspended at a final concentration of $2 \times 10^6$ viable AM/ml in RPMI 1640 (Gibco, Grand Island, N.Y.) containing 10 µg/ml E. coli endotoxin (026:B6, Sigma Co., St. Louis, Mo.), 100 U/ml penicillin (Flow Laboratories, McClean, Va.), 100 µg/ml streptomycin (Flow Laboratories), 2 mM L-glutamine (Flow Laboratories), and 50 µg/ml gentamicin. The cell suspension was plated in 150 cm$^2$ culture flasks at a density of $5 \times 10^5$ viable AM/cm$^2$ and incubated at 37° C. in 5% $CO_2$/air. After 24 hours the conditioned media were aspirated, quantitatively cultured on blood agar plates to assess bacterial contamination, and clarified by centrifugation at 10,000 x g for 30 min. Only samples that were free of bacterial growth were used in subsequent studies. The conditioned media were stored at −70°, C. for no more than 30 days.

The AM conditioned media were tested for chemotactic activity to porcine and human PMN. Human PMN were obtained by antecubital venipuncture and porcine PMN were obtained by subxiphoid cardiac puncture under general anesthesia. PMN were isolated by the method of Ferrante and Thong (*J. Immunol. Methods* 36: 109-117, 1980) using Mono-Poly Resolving Media (Flow Laboratories). PMN were resuspended in RPMI-1640 containing 5% heat inactivated fetal calf serum (Hyclone Laboratories, Inc., Logan, Utah) at a concentration of $3 \times 10^6$ cells/ml. Chemotaxis was measured by the modified Boyden technique using microchemotaxis chambers (Falk et al., *J. Immunol. Methods* 33: 239-247, 1980) (Neuroprobe Co., Bethesda, Md.). PMN (60 µl containing $1.8\% \times 10^5$ PMN) were added to the wells in the top compartment of the chamber. The sample to be tested was serially diluted in phosphate buffered saline containing 0.2% bovine serum albumin, pH 7.2, and 25 µl of sample was added to each well in the bottom compartment of the chamber. The top and bottom compartments of the chambers were separated by nitrocellulose filters (3.0 µm pore size, Neuroprobe, Inc., Cabin John, Md.). After incubation for 2 hours at 37° C. in 5% $CO_2$ and humidified air, the filters were removed and stained by a modified hematoxylin/eosin stain. PMN chemotaxis was measured as the total of cells at the end-point of migration in 10 high powered fields (x450) using a 5×5 mm eyepiece grid. The AM-conditioned media were found to contain chemotactic activity for both porcine and human PMN.

AMCF was purified from 500 ml of LPS-stimulated AM conditioned media, generated from $1.1 \times 10^9$ viable AM (equivalent to that of a single pig whole-lung lavage). A summary of the purification procedure showing the recovery at each step is shown in Table 1. All samples and column fractions were kept at 5° C. or frozen at −70° C. except during the two HPLC loading and elution steps, which were performed at room temperature. For the chemotaxis assay, aliquots of crude preparations and preparations containing high salt or low pH were brought to the appropriate assay conditions of ionic strength and pH either by dilution in PBS containing 0.2% BSA, pH 7.2 or by dialyzing them against the same solution at 5° C. using 3500 MW cutoff Spectra/por dialysis membranes (Spectrum Medical Industries, Los Angeles, Calif.) at 5° C. HPLC was performed on a Varian Vista 5500 liquid chromatograph, monitoring absorbance at either 280 nm or 215 nm on a Varian UV-200 ultra violet detector (Varian, Walnut Creek, Calif.).

TABLE 1

| Sample | Volume (ml) | Total Protein (mg) | Total Units | Specific Activity (unit/mg) |
| --- | --- | --- | --- | --- |
| Crude CM | 500 | 71.1 | 245000 | 3450 |
| Concentrated | 37 | 19.6 | 147000 | 7500 |
| SP-HPLC | 25 | 2.9 | 75000 | 25600 |
| RP-HPLC | 6 | 0.137 | 36100 | 264000 |
| AMCF-I | 1 | 0.074 | 30000 | 405000 |
| AMCF-II | 0.5 | 0.023 | 5000 | 217000 |

CM: conditioned media
SP-HPLC: sulfopropyl high performance liquid chromatography (TSK SP-5PW)
RP-HPLC: reversed-phase high performance liquid chromatography (C-4)
AMCF-I, AMCF-II: Alveolar Macrophage-derived Chemotactic Factor Peaks I and II (from RP-HPLC)
Total Units: refers to total units of neutrophil chemotactic activity, where total units = the reciprocal of the highest dilution of sample that maintained at least 3 times the baseline (negative control) activity times the volume of sample.

Human PMN were used for the detection of chemotactic activity during the course of the purification. Chemotactic activity was assayed essentially as described above. Serial dilutions of each sample were tested in quadruplicate wells in each experiment, and the results of the quadruplicate determinations were averaged. Zymosan activated human serum (HZAS) or zymosan activated porcine serum (PZAS) were prepared as described (Pillemer and Ecker, *J. Biol. Chem.* 137: 139–142, 1941; Pillemer et al., *J. Exp. Med.* 103: 1–13, 1956), diluted 1:10 in phosphate buffered saline containing 0.2% bovine serum albumin, pH 7.2 and included as a positive control in each chemotaxis assay. PBS containing 0.2% BSA, pH 7.2 served as a negative control. Chemotactic activity in units/ml was defined as the reciprocal of the highest dilution of sample that maintained at least 3 times the baseline (negative control) activity. Specific activity was expressed in chemotactic units/mg of total protein, where total protein was determined either by Folin phenol reagent (Lowry et al., ibid.), by absorbance at 280 nm ($A_{280}$ of 1.0 mg/ml solution = 1000) or by quantitative amino acid analysis.

0.5 liter of crude conditioned media was adjusted to pH 3.5 and clarified by centrifugation. The solution was then passed through a 2.5×4 cm column of SP-Sephadex C-25 equilibrated in 10 mM acetic acid/Na acetate, pH 3.5 at 5° C. The column was washed until the eluate reached baseline absorbance, then the adsorbed protein was eluted with a small volume of 100 mM potassium phosphate buffer containing 1.0 M NaCl at pH 7.0. 98% of the absorbance units loaded onto the column was recoverd in the pass-through and gradient fractions. There was no detectable chemotactic activity in the wash-through fractions. All of the detectable chemotactic activity was localized to the single eluting protein peak. This step accomplished both a 10-fold concentration and a 2-fold purification.

The chemotactically active fractions from the SP-Sephadex column were combined and dialyzed against 8 liters of 10 mM acetic acid/Na acetate, pH 3.5 for 12 hours. The dialyzed sample was then loaded onto a 75×7.5 cm column of TSK SP-5PW (Bio-Rad Laboratories, Richmond, Calif.) equilibrated in 10 mM acetic acid/Na acetate, pH 3.5. The column was eluted at a flow rate of 1.0 ml/minute using two different gradients in sequence. Over the first 20 minutes a linear salt gradient was used with a limit buffer of 10 mM acetate, containing 1 M NaCl pH 3.5. Over the next 20 minutes a "linear" pH gradient was programmed with a limit buffer of 100 mM potassium phosphate containing 1M NaCl, pH 7.0. 1.0 ml fractions were collected over the 40 minutes of gradient elution. The elution profile using sequential salt and pH gradients is shown in FIG. 1. 93% of the total protein loaded onto the column was recovered in the pass-through and gradient fractions. There was no detectable activity in the pass-through fractions. Only the final peaks (fractions 56–64) contained chemotactic activity. This step accomplished a 5-fold purification.

Figure 2A:
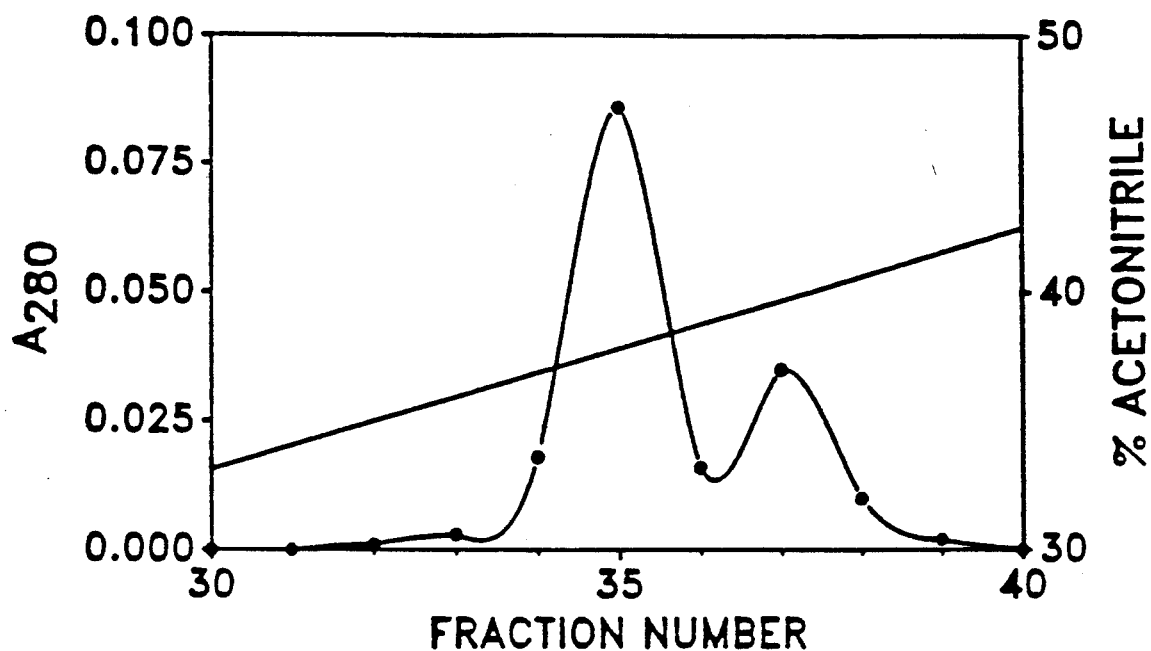
FIGS. 2A-B illustrates the results of reversed-phase HPLC fractionation of a partially purified chemotactic protein composition. The top panel shows the acetonitrile elution gradient and the $A_{280}$ of the eluate. The bottom panel shows the chemotactic activity and gel electrophoresis patterns of column fractions.
Figure 2B:
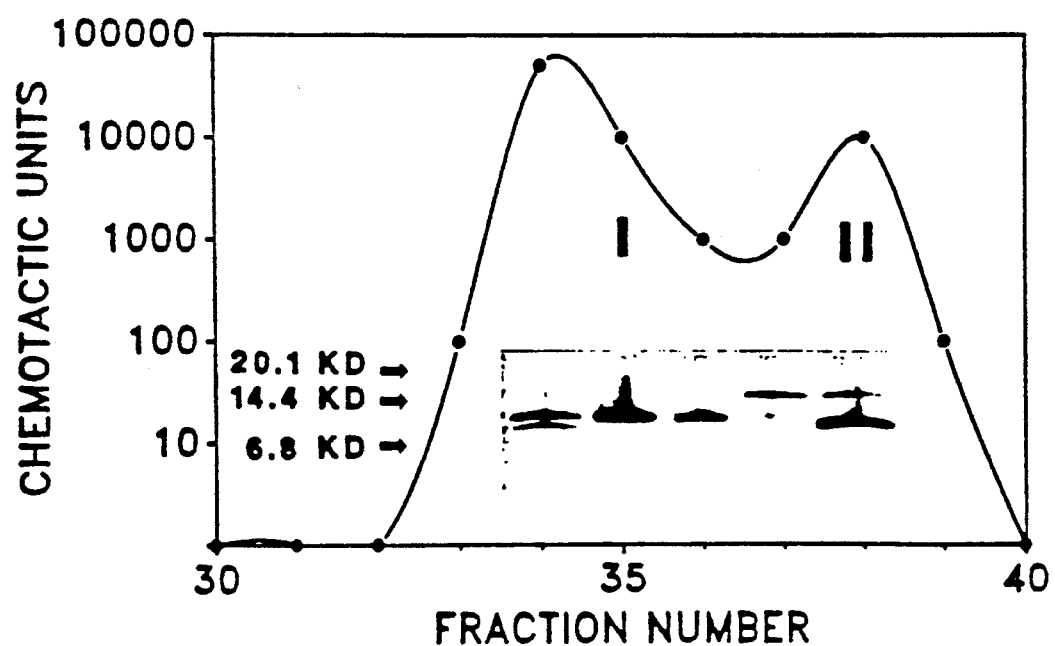

Chemotactically active fractions 56–64 from SP-5PW chromatography were combined, acidified by 1:2 dilution in 0.1% TFA, and loaded onto a C-4 reversed-phase HPLC column equilibrated in 0.1% trifluoroacetic acid (TFA) in 5% acetonitrile. The column was eluted with a linear gradient over 35 minutes using a limit solution of 0.1% TFA in 80% acetonitrile. 0.5 ml fractions were collected at a flow rate of 1 ml/minute. The elution profile is shown in FIG. 2. 85% of the total protein loaded onto the column was recovered in the pass-through and gradient fractions. The pass-through fractions and every gradient fraction were assayed for chemotactic activity. Two peaks of activity eluted between 35% and 45% acetonitrile, and were designated AMCF-I and AMCF-II. They were separated by two tubes that lacked chemotactic activity.

10 μl aliquots of every fraction from the C-4 HPLC were evaporated to dryness, redissolved in Laemmli buffer under reducing or non-reducing conditions, boiled for 5 minutes, and applied to an 8–25% polyacrylamide gradient gel (Pharmacia, Piscataway, N.J.). Electrophoresis was carried out using a Phast-Gel system (Pharmacia) for 65 volt-hours at 20 mA/gel. Molecular weight standards included a mixture of recombinant human insulin (Humulin, Eli Lilly and Co., Indianapolis, Ind.) (6.2 kDa), albumin (67 kDa), ovalbumin (43 kDa), carbonic anhydrase (30 kDa), trypsin inhibitor (20.1 kDa), and alpha-lactalbumin (14.4 kDa) Molecular weights of AMCF-I and AMCF-II were estimated from a plot of Rf vs log10(molecular weight) to be 10 kDa. FIG. 2 shows a composite of the $A_{280}$, chemotactic activity, and SDS-PAGE profile of material eluting between 35% and 45% aceto itrile.

Figure 3:
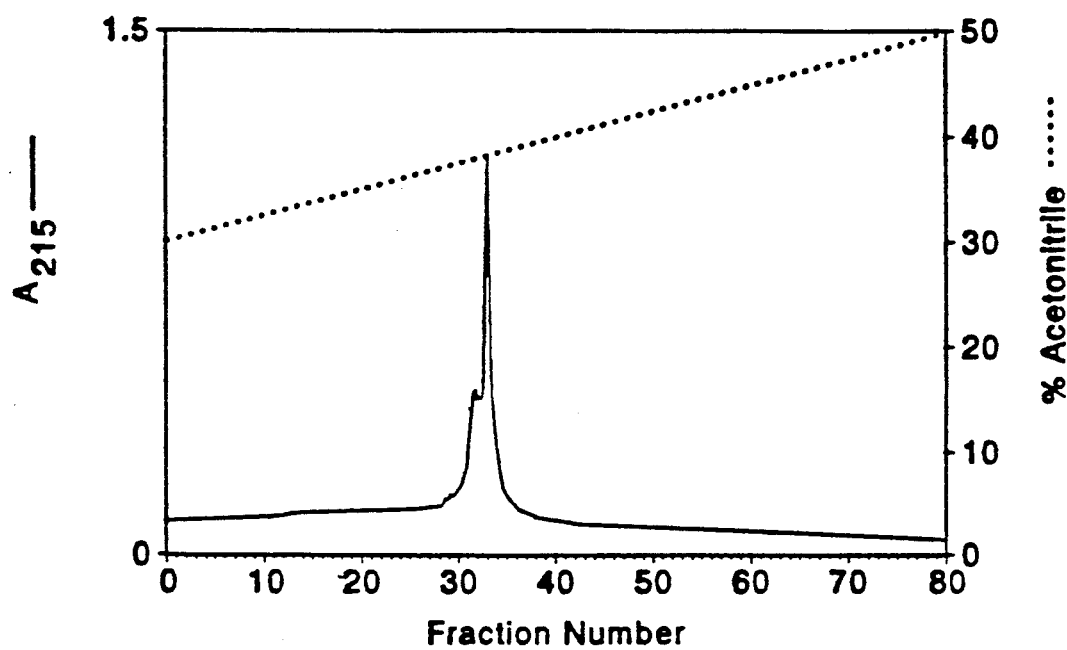
FIG. 3 illustrates the final purification of AMCF-II.

AMCF-II was further purified by rechromatography of fraction 38 (FIG. 2) on C-4 reversed-phase HPLC using a more shallow gradient and a smaller fraction volume (FIG. 3). The resulting electrophoretically pure AMCF-II (fraction 35 in FIG. 3) was used for subsequent characterization.

Example 2—Protein Characterization

Chemotactic Dose-Response

Figure 4A:
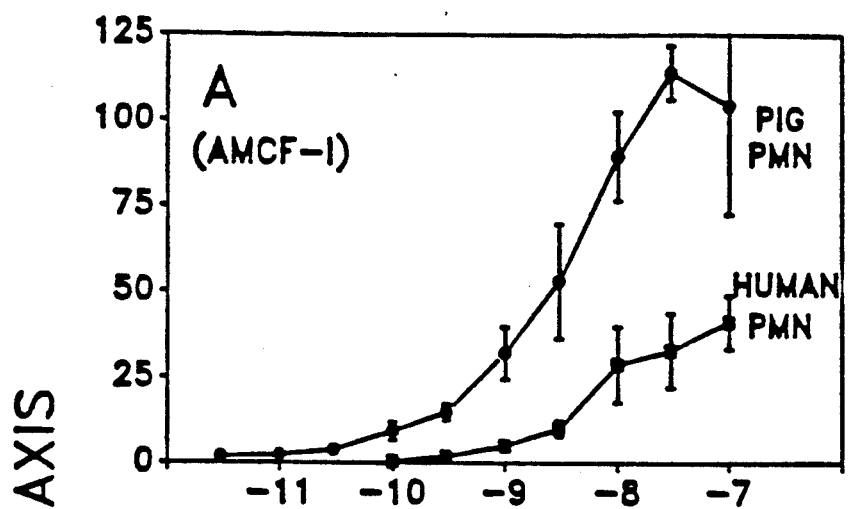
FIGS. 4A-B illustrates chemotactic dose-reponse curves of AMCF-I (A) and AMCF-II (B) for human and porcine neutrophils.
Figure 4B:
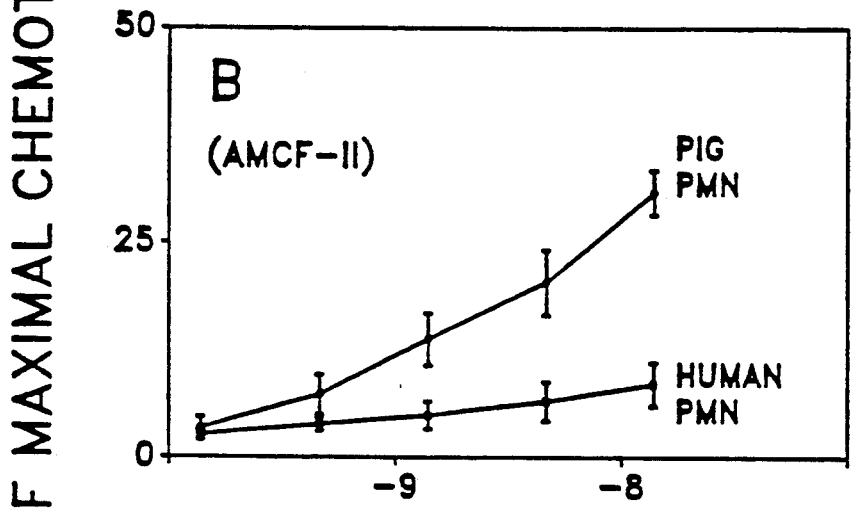
Figure 4C:
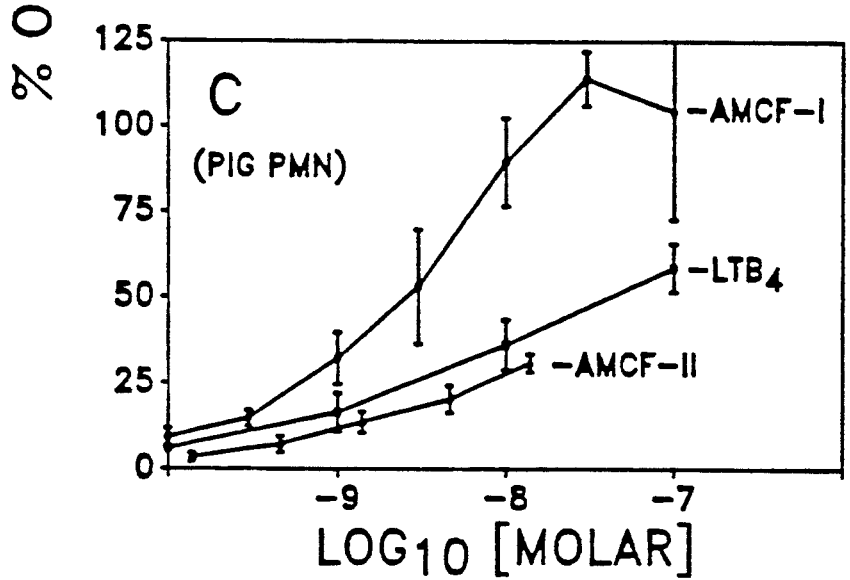
FIG. 4C shows a comparison of the dose-response curves of AMCF-I, AMCF-II and $LTB_4$ for porcine neutrophils. Results are expressed as a percentage of the maximal response to the species-specific zymosan-activated serum.

The chemotactic dose-responses of AMCF-I and AMCF-II for porcine and human PMN are compared in FIGS. 4A–C. AMCF-I attracted both porcine and human PMN. The lowest concentration of AMCF-I with significant chemotactic activity was $3 \times 10^{-10}$M for porcine PMN, and $3 \times 10^{-9}$M for human PMN. The peak chemotactic activity of AMCF-I occured at $3 \times 10^{-8}$M for porcine PMN, and at or above $1 \times 10^{-7}$M for human PMN (FIG. 4A).

In contrast, AMCF-II attracted porcine PMN, but had very little effect on human PMN (FIG. 4B). The lowest concentration of AMCF-II with significant chemotactic activity was near $1 \times 10^{-9}$M. AMCF-II had significant chemotactic activity for human PMN in only one of three separate experiments.

FIG. 4C compares the dose-responses of AMCF-I, AMCF-II, and LTB4. The peak chemotactic activity of AMCF-I exceeded 100% of that observed with simultaneously tested zymosan-activated porcine serum. AMCF-II demonstrated a dose-response relationship with a slope similar to that observed with LTB4.

In vivo PMN Chemotaxis

A healthy 19 kg Yorkshire pig was sedated with xylazine and ketamine and anesthetized with 100 mg sodium thiopental administered intravenously. A fiberoptic bronchoscope was passed transorally and the tip wedged in either the lingula (control side) or the right middle lobe (experimental side). 10 ml of a $10^{-9}$M solution of AMCF-I was prepared as follows: 10 µl of fraction #34 from reversed-phase HPLC (FIG. 2) was diluted to 1.0 ml with sterile phosphate buffered saline containing 0.2% bovine serum albumin, pH 7.2. Immediately before instillation, the solution was further diluted to 10 ml in pyrogen-free 0.9% NaCl. A control solution without AMCF-I was prepared by diluting 10 µl of 0.1% TFA in 40% acetonitrile to 1.0 ml with sterile phosphate buffered saline containing 0.2% bovine serum albumin, pH 7.2, then further diluting the solution to 10 ml in pyrogen-free 0.9% NaCl. The 10 ml solutions were instilled, immediately followed by five 10 ml aliquots of air to disperse the aliquot of fluid in the lung segment. Four hours later, the pig was again sedated and anesthetized. Bronchoalveolar lavage was performed on each of the lung segments with the fiberoptic bronchoscope using five 30 ml aliquots of pyrogen-free 0.9% NaCl. Each lavage aliquot was collected with gentle suction. Total cell counts in the lavage fluid were determined on cytospin preparations of lavage fluids stained with Diff-Quik (American Scientific Products, McGaw Park, Ill.). The total and differential cell counts are shown in Table 2. The instillation of AMCF-I produced a 20-fold increase in total recovered cells and a 250-fold increase in total recovered PMN over control. In addition, AMCF-I also caused a 10-fold increase in AM and a 25-fold in lymphocytes.

TABLE 2

| Instillate | Lung Lobe | Volume (ml) | Total Cells ($\times 10^6$) | AM ($\times 10^6$) | PMN ($\times 10^6$) | Lymph ($\times 10^6$) |
|---|---|---|---|---|---|---|
| AMCF-I | RML | 136 | 1370 | 562 | 671 | 137 |
| CONTROL | LINGULA | 129 | 66.4 | 58.4 | 2.7 | 5.3 |
| FOLD INCREASE = | | | 20.6 | 9.6 | 249 | 25.8 |

Figure 5A:
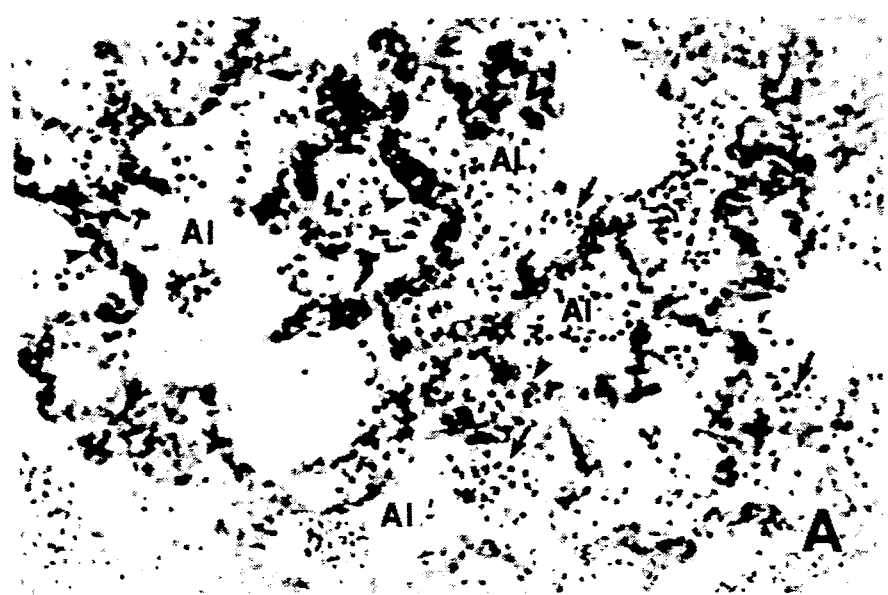
FIGS. 5A-B shows comparative micrographs of lung biopsies after instilling AMCF-I (A) or vehicle only (B). A control lung segment is shown in FIG. 5C. In the AMCF-I instilled lobe, neutrophils (arrows) are present in the alveolar airspace (AI) and in the lung interstitium.
Figure 5B:
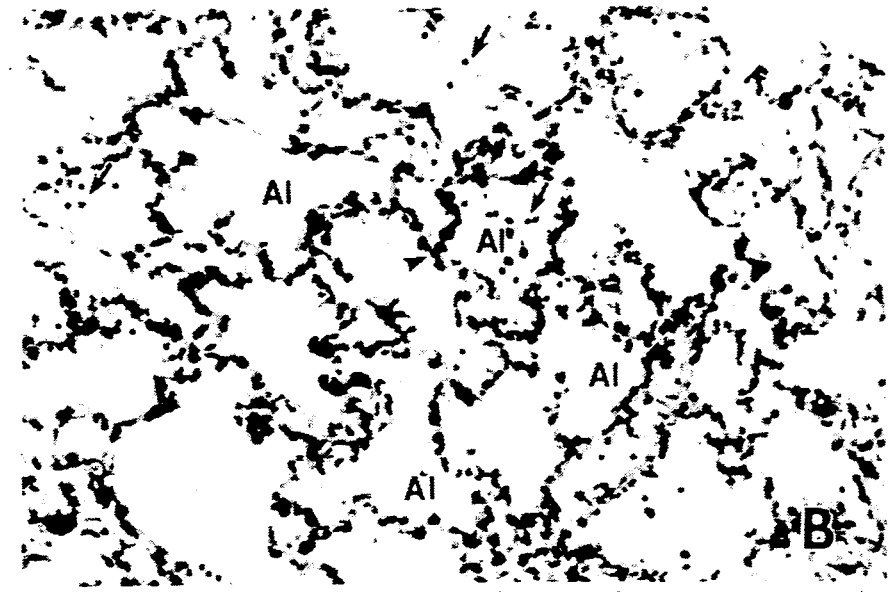
Figure 5C:
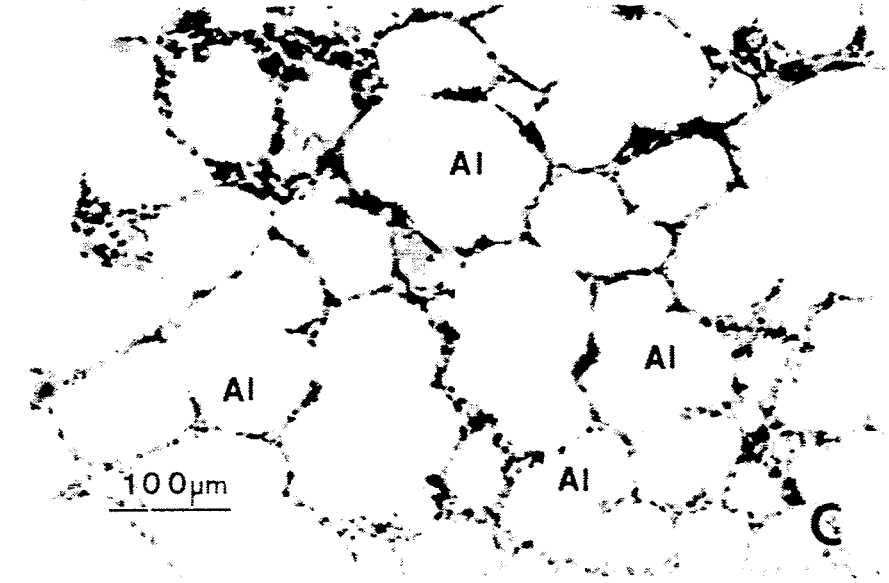

AMCF-I: Alveolar Macrophage-derived Chemotactic Factor Peak 1
CONTROL: A solution containing everything except AMCF-I (see text)
RML: right middle lobe
AM: alveolar macrophage
PMN: polymorphonuclear leukocyte
LYMPH: lymphocyte Histopathologic sections of the lung segments are shown in FIG. 5. For histopathology, open lung biopsies of the lingula and right middle lobe were performed via a median sternotomy incision. Lung tissue was fixed in formalin and embedded in paraffin, and sections were stained with hematoxylin and eosin for light microscopy. The experimental lung segment where AMCF-I was instilled (right middle lobe) showed a marked infiltration of inflammatory cells, predominately PMN, which involved the pulmonary interstitium as well as the alveolar airspaces (FIG. 5A). The control lung segment (lingula) is shown for comparison and had a normal appearance (FIG. 5C).

AMINO ACID COMPOSITION AND SEQUENCE ANALYSIS

Samples for amino acid composition analysis were degraded by vapor phase hydrolysis over 5.7N constant boiling HCl for 24 hours. Two 2 µg samples of AMCF-I and two 0.5 µg samples of AMCF-II were hydrolysed and all four samples were run separately on a Beckman System 6300 High Performance amino acid analyzer (Beckman Instruments, Palo Alto, Calif.). Amino acid composition analyses of unmodified AMCF-I and AMCF-II are shown in Table 3. Their compositions are distinctly different. Both are devoid of tyrosine. AMCF-I has no methionine and AMCF-II has no phenylalanine.

TABLE 3

| | Residues per Molecule* | |
|---|---|---|
| AMINO ACID | AMCF-I | AMCF-II |
| ASP | 5.8 | 7.1 |
| THR | 4.4 | 5.5 |
| SER | 4.8 | 5.1 |
| GLX | 19.8 | 10.3 |
| PRO | 5.1 | 7.6 |
| GLY | 4.0 | 6.8 |
| ALA | 3.4 | 9.7 |
| CYS | ND | ND |
| VAL | 10.0 | 6.8 |
| MET | 0 | 2.5 |
| ILE | 6.2 | 6.7 |
| LEU | 7.1 | 8.4 |
| TYR | 0 | 0 |
| PHE | 4.3 | 0 |
| HIS | 3.7 | 2.4 |
| LYS | 11.1 | 13.1 |
| ARG | 5.7 | 5.9 |
| TRP | ND | ND |

*Estimations based on SDS-PAGE derived molecular weights.
Quantities of cysteine and tryptophan were not determined (ND).

N-terminal sequence anaysis was determined by Edman degradation of 10 µg samples of both AMCF-I and AMCF-II with an automated gas phase peptide sequenator (model 475A Pulse Liquid Protein Sequencer; Applied Biosystems, Inc., Foster City, Calif.). Cycles with no detectable PTH derivatives were assigned to cysteine. The sequences of the first 20 amino acids of unmodified AMCF-I and the first 30 amino acids of unmodified AMCF-II are shown in Table 4. X indicates an amino acid tentatively identified as cysteins as described above.

TABLE 4

AMCF-I:
Ala—Arg—Val—Ser—Ala—Glu—Leu—X—Arg—Gln—X—Ile—Asn—Thr—His—Ser—Thr—Pro—Phe—His

AMCF-II:
Ser—Pro—Ile—Glu—Ala—Ala—Glu—Ala—Ala—Val—Val—Arg—Glu—Leu—Arg—X—Met—X—Leu—Thr—Thr—Thr—Pro—Gly—Ile—His—Phe—Lys—Met—Ile

No other proteins with these unique amino acid sequences were found in a computer search of the EMBL, GenBank, Swissprot, and PIR databases using the FASTA and tFASTA (Pearson and Littman, Proc. Natl. Acad. Sci. USA 85: 2442-2448, 1988) programs. Although AMCF-I and AMCF-II are clearly distinct, there are homologies between them. In addition there are homologies to specific regions of other proteins which also exhibit chemotactic activity for neutrophils (FIG. 6, upper panel). The best fit alignment of these proteins shows remarkable conservation of two cysteine residues that are in close proximity. These cysteine residues correspond to the two blank cycles in the Edman degradation of unmidified AMCF-I and AMCF-II. This homology comparison suggests the assignment of Cys to these unidentified positions in the sequences of both AMCF-I and AMCF-II as shown in FIG. 6.

Remarkable homology was also evident in close proximity to these cysteine residues, as illustrated in FIG. 6. In addition, secondary structure analysis of all these peptides using the algorithm of Leszczynski and Rose (*Science* 234: 849-855, 1986) suggests the presence of an Omega loop in the regions of these molecules corresponding to AMCF-I residues 13-18.

Although the foregoing invention has been described in some detail by way of illustration and example for purposes of clarity and understanding, it will be apparent that certain changes and modifications may be practiced within the scope of the appended claims.

I claim:

1. Substantially pure porcine AMCF-I having the following characteristics:
   an amino-terminal sequence Ala-Arg-Val-Ser-Ala-Glu-Leu;
   a molecular weight of approximately 10 kD as determined by polyacrylamide gel electrophoresis;
   an amino acid composition as follows:

| Amino Acid | Mole % |
|---|---|
| Asp | 6.1 |
| Thr | 4.6 |
| Ser | 5.0 |
| Glx | 20.8 |
| Pro | 5.3 |
| Gly | 4.2 |
| Ala | 3.6 |
| Val | 10.5 |
| Met | 0.0 |
| Ile | 6.5 |
| Leu | 7.4 |
| Tyr | 0.0 |
| Phe | 4.5 |
| His | 3.9 |
| Lys | 11.6 |
| Arg | 6.0 | as determined by acid hydrolysis, wherein Cys and Trp are not accounted for; and
exhibits chemotactic activity for porcine and human neutrophils.

2. AMCF-I according to claim 1 having a specific activity of at least approximately 200,000 units/mg.

3. AMCF-I according to claim 1 having a specific activity of at least 400,000 units/mg.

* * * * *